US00PP22631P2

(12) United States Plant Patent
Probst

(10) Patent No.: US PP22,631 P2
(45) Date of Patent: Apr. 3, 2012

(54) ***COREOPSIS* PLANT NAMED 'CHA CHA CHA'**

(50) Latin Name: ***Coreopsis* hybrid**
Varietal Denomination: Cha Cha Cha

(76) Inventor: Darrell R. Probst, Hubbardston, MA (US)

( * ) Notice: Subject to any disclaimer, the term of this patent is extended or adjusted under 35 U.S.C. 154(b) by 245 days.

(21) Appl. No.: 12/660,480

(22) Filed: Feb. 26, 2010

(51) Int. Cl.
*A01H 5/00* (2006.01)

(52) U.S. Cl. ..... Plt./417

(58) Field of Classification Search ..... Plt./417
See application file for complete search history.

(56) References Cited

U.S. PATENT DOCUMENTS

| | | | | |
|---|---|---|---|---|
| PP12,720 | P2 * | 6/2002 | Leonard | Plt./417 |
| PP16,923 | P2 * | 8/2006 | Schweizer | Plt./417 |
| PP21,869 | P2 * | 4/2011 | Probst | Plt./417 |
| PP22,015 | P2 * | 7/2011 | Probst | Plt./417 |
| PP22,129 | P2 * | 9/2011 | Probst | Plt./417 |
| PP22,130 | P2 * | 9/2011 | Probst | Plt./417 |
| PP22,131 | P2 * | 9/2011 | Probst | Plt./417 |

OTHER PUBLICATIONS

UPOV ROM GTITM Computer Database, GTI Jouve Retrieval Software 2011/10 Citation for 'Cha Cha Cha'.*

* cited by examiner

*Primary Examiner* — Wendy C Haas
(74) *Attorney, Agent, or Firm* — Penny J. Aguirre

(57) ABSTRACT

A new cultivar of hybrid *Coreopsis* named 'Cha Cha Cha' characterized its inflorescences with ray florets that are gold in color with a small dark red eye zone, its bushy and relatively short plant habit, its floriferous and long blooming habit, its relative sterility, and its vigorous growth habit.

2 Drawing Sheets

Botanical classification: *Coreopsis* hybrid.
Variety denomination: 'Cha Cha Cha'.

CROSS REFERENCE TO A RELATED APPLICATION

This application is co-pending with five other U.S. Plant Patent Applications filed for plants derived from similar parentage ins the Inventor's breeding program. The co-pending applications are drawn to the following plants: 'Caliente' (U.S. Plant Pat. No. 21,869), 'Salsa' (U.S. Plant Pat. No. 22,129), 'Limbo' (U.S. Plant Pat. No. 22,130), 'Mambo' (U.S. Plant Pat. No. 22,131), and 'Jive' (U.S. Plant Pat. No. 22,015).

BACKGROUND OF THE INVENTION

The present invention relates to a new and distinct cultivar of *Coreopsis* plant, botanically of hybrid origin and known as *Coreopsis* 'Cha Cha Cha' and will be referred to hereinafter by its cultivar name, 'Cha Cha Cha'. The new cultivar of *Coreopsis* is an herbaceous annual grown for use in borders and containers.

The new invention arose from an ongoing controlled breeding program in Hubbardston, Mass. The objective of the breeding program is to develop hybrid cultivars of *Coreopsis* with unique and superior garden attributes. The Inventor crossed *Coreopsis* 'Sweet Dreams' (U.S. Plant Pat. No. 12,720) and *Coreopsis rosea* with *Coreopsis tinctoria* and another annual type species that are not commercialized and made six generations of crosses to produce interspecific hybrids to utilize in his breeding work. The new variety was developed with a goal of producing new cultivars of *Coreopsis* with unique flower colorations, short and bushy plant habits, and sterility to lengthen bloom periods.

The Inventor made a controlled cross in August 2006 in his test garden in Hubbardston, Mass. between an unnamed F6 generation seedling produced with crosses of *Coreopsis tinctoria* and *Coreopsis rosea* as the female parent and an unnamed F6 generation seedling produced with crosses of unnamed hybrid *Coreopsis* from his breeding program and *Coreopsis rosea* as the male parent. 'Cha Cha Cha' was selected in August 2007 as a single unique plant amongst the resulting seedlings.

Asexual reproduction of the new cultivar was first accomplished by stem cuttings in Kensington, Conn. in August of 2007 under the direction of the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Cha Cha Cha' as unique from all *Coreopsis* cultivars and species known to the Inventor.

1. 'Cha Cha Cha' exhibits composite inflorescences with ray florets that are gold in color with a small dark red eye zone.
2. 'Cha Cha Cha' exhibits a bushy plant habit and is relatively short in height; reaching 12 to 18 inches (30 to 45 cm) in height.
3. 'Cha Cha Cha' exhibits a vigorous growth habit.
4. 'Cha Cha Cha' exhibits a long blooming period with an abundance of blooms; blooming from June through August in Massachusetts.

5. 'Cha Cha Cha' is relatively sterile and produces very few seeds if any.

The female parent differs from 'Cha Cha Cha' in having a shorter plant height (reaching 8 to 12 inches in height), in having inflorescences with ray florets that are white in color with a small burgundy eye, and in producing an abundance of seed that shortens its bloom season to one month. The male parent differs from 'Cha Cha Cha' in being taller in plant height (reaching 18 to 24 inches in height), in being less floriferous and in having inflorescences with ray florets that are solid gold in color. 'Cha Cha Cha' can be most closely compared to cultivars from the same parentage, 'Jive' and 'Salsa'. They are both similar to 'Cha Cha Cha' in plant habit and blooming habit. 'Jive' differs from 'Cha Cha Cha' in having inflorescences with ray florets that are white in color with a large dark burgundy-purple eye zone. 'Salsa' is similar to 'Cha Cha Cha' in having inflorescences with ray florets that are gold in color with a red eye zone, however 'Salsa' differs from 'Cha Cha Cha' in having ray florets with a larger sized eye zone.

BRIEF DESCRIPTION OF THE DRAWING

The accompanying colored photographs illustrate the overall appearance and distinct characteristics of the new *Coreopsis*.

The photograph in FIG. 1 was taken in late summer of two five month-old plants of 'Cha Cha Cha' as grown outdoors in a mixed container planting in New Hope, Minn. and illustrates the bushy plant habit and floriferous blooming habit of 'Cha Cha Cha'.

Figure 1:
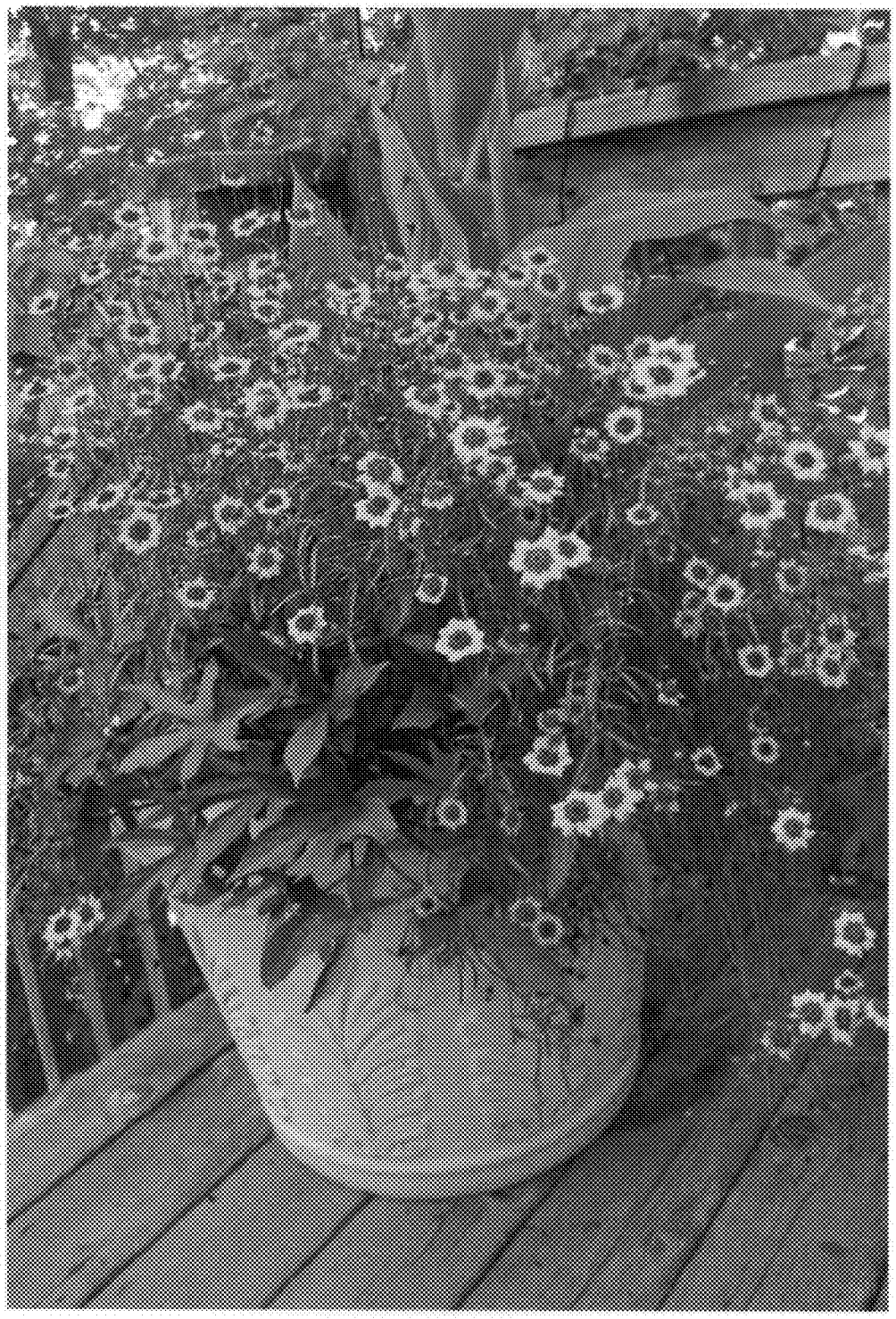
Figure 2:
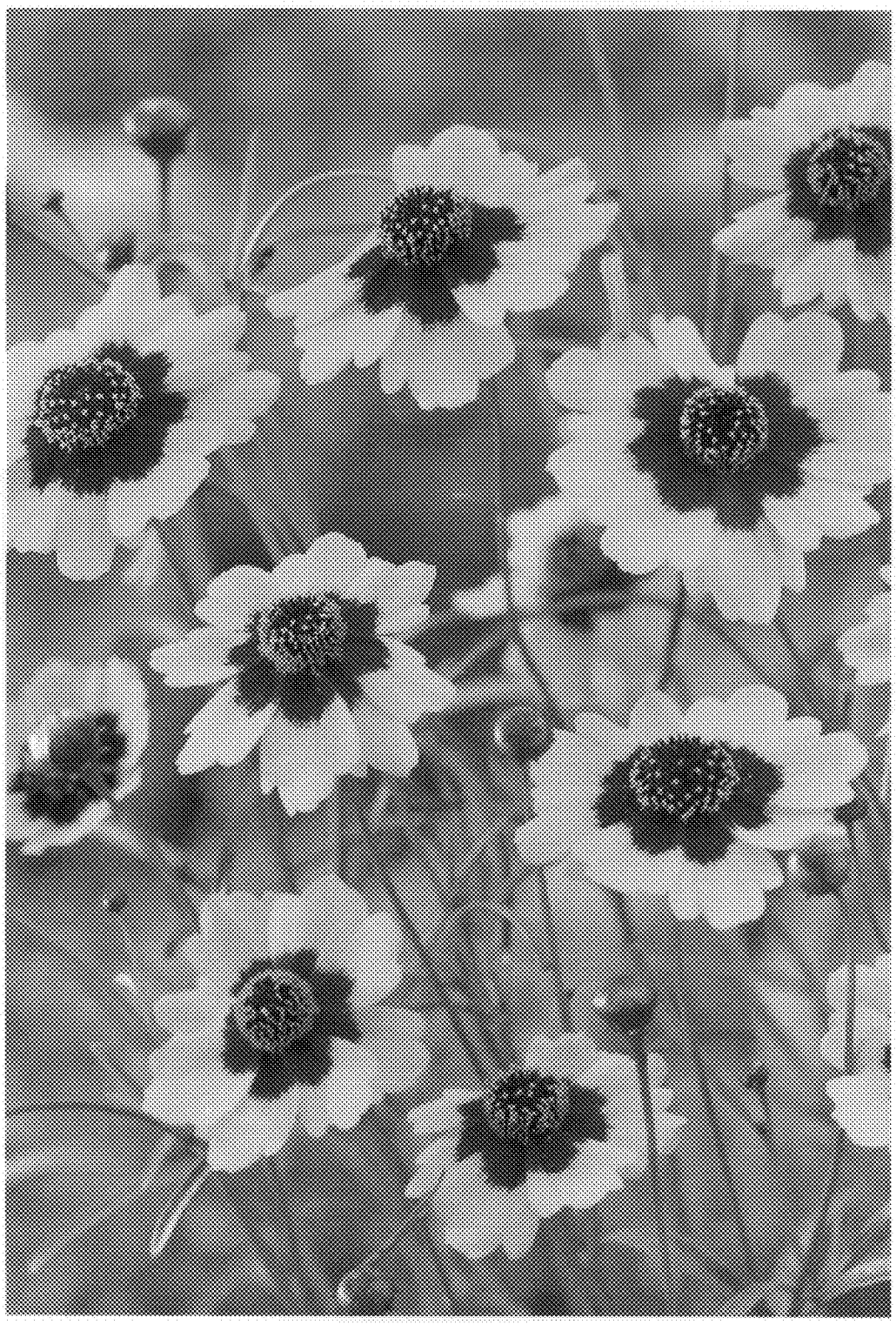

The photograph in FIG. 2 was taken in late summer of a six month-old plant of 'Cha Cha Cha' as grown outdoors in a two-gallon container in The Netherlands and provides a close-up view of inflorescences of 'Cha Cha Cha'. The Colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three growing seasons in a trial garden in Hubbardston, Mass. with the detailed botanical data collected from five month-old plants of the new cultivar as grown in two-gallon containers in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from June through August in central Massachusetts.

*Plant habit*.—Herbaceous annual, well-branched to produce a bushy habit.

*Height and spread*.—Reaches 12 to 18 inches (30 to 45 cm) in height and 12 to 15 inches (30 to 38 cm in width) in 3 months from a rooted cutting.

*Cold hardiness*.—Has not been tested as it is grown as an annual.

*Diseases resistance*.—No particular resistance or susceptibility has been observed.

*Root description*.—Fibrous, fine and well-branched.

Growth and propagation:

*Propagation*.—Terminal stem cuttings.

*Growth rate*.—Vigorous.

Stem description:

*Shape*.—Oval, solid.

*Stem color*.—146C.

*Stem size*.—Main stem averages 17 cm in length with laterals an average of 19 cm in length (excluding peduncles), an average of 2.5 mm in width.

*Stem surface*.—Very finely puberulent with some ridges.

*Branching habit*.—An average of 6 basal branches with an average of 4 lateral branches, and 3 terminal flowering branches on each lateral, branch internode is variable but typically about 5 cm.

Foliage description:

*Leaf division*.—Simple.

*Leaf margins*.—Tri-lobed, entire or five-lobed.

*Leaf size*.—Up to 7 cm in length and 3.6 cm in width when five-lobed with side lobes 1.7 cm in length and 2 mm in width.

*Leaf shape*.—Fan-shaped overall when tri-lobed, elliptic in shape when five-lobed, with lobes narrowly lanceolate to linear.

*Leaf base*.—Attenuate.

*Leaf apex*.—Acute.

*Leaf venation*.—Pinnate, not prominent, vein color matches leaf color.

*Leaf attachment*.—Sessile.

*Leaf arrangement*.—Opposite.

*Leaf internode length*.—Variable, an average of 6 cm.

*Leaf quantity*.—An average of 18 per lateral stem.

*Leaf surface*.—Dull and very finely puberulent on upper surface and lower surface.

*Leaf color*.—Young and mature upper surface; 137A, young and mature lower surface; 137B.

Flower description:

*Inflorescence type*.—Composite with ray florets surrounding disk florets in the center forming a radiant head, inflorescences are borne singular to group of 3 at terminal of lateral branches.

*Lastingness of inflorescence*.—About one week until senescence of ray flowers, bracts and disk flowers are persistent.

*Fragrance*.—None detected.

*Quantity of inflorescences*.—An average of 20 per lateral branch.

*Inflorescence size*.—Average 1 cm in depth and up to 2.5 cm in diameter with disk portion an average of 8 mm in diameter.

*Inflorescence buds*.—Average of 5 mm in depth and 4 mm in diameter, shape is spherical but flattened, color is a blend of 23A and 146B, with bracts 146B.

*Peduncle*.—Average of 6 cm in length and 1 mm in diameter, 137B in color, finely puberulent surface.

Involucral bracts:

*Bract number*.—Three rows of 5, one row of outer bracts and two rows of inner bracts.

*Bract arrangement*.—Outer bracts are un-fused spreading and slightly cupped upward, inner bracts overlap and surround receptacle with a campanulate form with apical portion un-fused, spreading, and held close to ray florets.

*Bract size*.—Outer bracts about 2 mm in length and 1.5 mm in width, inner bracts about 6 mm in length and 3 mm in width with free portion an average of 3 mm in length and 3 mm in width.

*Bract color*.—Outer bracts 137B in both surfaces, inner bracts; fused portion 137B, unfused portion is a blend of 23A and 147A.

*Bract texture*.—Outer bract; puberulent, waxy, inner bracts glabrous and waxy.

*Bract apex*.—Outer bract; acute, inner bracts; acute.

*Bract base*.—Truncate.

*Bract shape*.—Outer bracts; ovate, inner bracts; free portion broadly ovate.

Ray florets (sterile):

*Number*.—8.

*Shape*.—Ovate, appearance of three longitudinal sections with center section longer.

*Size*.—Average of 1 cm in length and 7 mm in width.

*Apex*.—Emarginate.

*Base*.—Broadly cuneate.

*Margins*.—Entire on sides, divided into 3 lobes at apex with apex of lobes rounded and center lobe emarginate.

*Aspect*.—Held nearly horizontal and slightly cupped upward.

*Surface*.—Glabrous on both surfaces.

*Color*.—Upper surface opening and fully open; lower one third 59A with upper half 12A, lower surface opening and fully open; 12B slightly suffused with 177A.

Disk flowers (male and female):

*Shape*.—Tubular, corolla is fused, flared at apex.

*Size*.—About 5 mm in length and 0.7 mm in width.

*Color*.—In masse; when fully open 200B with tips 7A and N25B, corolla; base (tube) is 163B, flared portion is N77A and translucent.

*Receptacle*.—About 4 mm in diameter and 1 mm in depth, 144B in color.

Reproductive organs:

*Presence*.—Disk flowers are perfect, ray flowers are sterile.

*Gynoecium*.—1 Pistil, 3.5 mm in length, style is very fine and about 160A in color and translucent, bifid pilose stigma is N25B in color and changing to 7A with branches about 1 mm in length and recurved, ovary is 1 mm in length, 0.5 mm in width, inferior, and 145D in color.

*Androcoecium*.—5 stamens, fused into tube surrounding style, 1.5 mm in length and 0.3 mm in width, about 200A in color, pollen is abundant in quantity and 7A in color.

*Fruit/seed*.—Relatively sterile and produces very few seeds if any.

It is claimed:

1. A new and distinct cultivar of *Coreopsis* plant named 'Cha Cha Cha' as herein illustrated and described.

* * * * *